United States Patent [19]
Purdom

[11] Patent Number: 6,123,849
[45] Date of Patent: Sep. 26, 2000

[54] CHROMATOGRAPHIC COLUMN AND VALVE

[75] Inventor: Geoffrey John Purdom, Oxfordshire, United Kingdom

[73] Assignee: Millipore Corporation, Bedford, Mass.

[21] Appl. No.: 09/284,717

[22] PCT Filed: Oct. 27, 1997

[86] PCT No.: PCT/GB97/02943

§ 371 Date: May 21, 1999

§ 102(e) Date: May 21, 1999

[87] PCT Pub. No.: WO99/22234

PCT Pub. Date: May 6, 1999

[51] Int. Cl.$^7$ .................................................. B01D 15/08
[52] U.S. Cl. ...................... 210/656; 210/659; 210/198.2; 210/281
[58] Field of Search ................................... 210/656, 659, 210/198.2, 281; 95/82, 85; 96/101, 103, 105

[56] References Cited

U.S. PATENT DOCUMENTS

| 5,213,683 | 5/1993 | Mann | 210/198.2 |
| 5,282,973 | 2/1994 | Mann | 210/656 |
| 5,902,485 | 5/1999 | Davis | 210/656 |

FOREIGN PATENT DOCUMENTS

| 96/10451 | 4/1996 | WIPO | 210/198.2 |

*Primary Examiner*—Ernest G. Therkorn
*Attorney, Agent, or Firm*—Nields, Lemack & Dingman

[57] ABSTRACT

A chromatography column having at least one central slurry valve positioned at either the top cell assembly and/or the bottom cell assembly. The central slurry valves have a pneumatically actuated valve sleeve which can be shifted to create two different flow configurations. One flow configuration allows for the simultaneous cleaning in place of the flow path used to charge the column with chromatography media and the separate processing of fluid through the chromatography media. The other flow configuration permits the reslurrying and removal of chromatography media from the column, and the subsequent repacking of the column with fresh chromatography media without disassembling the column and the provision of venting the column in the event of overpressurization during packing.

15 Claims, 4 Drawing Sheets

CHROMATOGRAPHIC COLUMN AND VALVE

REFERENCE TO RELATED APPLICATIONS

This application is a 371 of PCT/GB97/02943 filed Oct. 27, 1997.

The present invention relates to a chromatography column.

Frequently it is desirable to separate out one or more useful components from a fluid mixture that contains other components which may not be useful or are less valuable. To accomplish this it is often necessary or desirable to fractionate such a fluid mixture to separate out the useful or desired components. This can be carried out by using liquid chromatography systems. Liquid chromatography may briefly be described as the fractionation of components of a mixture based on differences in the physical or chemical characteristics of the components. The various liquid chromatographic systems fractionate the components with a fractionation matrix. Some liquid chromatographic matrix systems fractionate the components of a mixture based upon such physical parameters as molecular weight. Still other liquid chromatographic systems will fractionate the components of a mixture based upon such chemical criteria as ionic charge, hydrophobicity, and the presence of certain chemical moieties such as antigenic determinants or lectin-binding sites on the components.

Chromatography systems of various sized are used in both laboratory analysis operations and for industrial scale production operations in which separation steps such as separating out a fraction from human blood or separating out impurities from a pharmaceutical can be carried out on a large scale in a batch process.

The development of chromatography columns has aimed at providing ease of operation and various additional benefits which have particular commercial importance. These include: (a) the ability to be sterilized by autoclaving; (b) improved sanitation by virtue of design features giving less carryover of product from one batch to the next; (c) the ability to resist solvents; (d) material conformity to food grade FDA regulations; (e) an improved pressure tolerance; (f) lower cost; and (g) the potential for full or partial automation.

Traditionally, a chromatography column must be disassembled to reslurry and remove chromatography media in order to repack the chromatography column with fresh chromatography media or with different chromatography media specific for an application. This procedure has several problems. First, the time required to perform this operation is substantial, especially with large industrial columns, and results in lost productivity in a commercial operation. Second, the constant assembly and disassembly of the chromatography column creates excessive wear on the components and leads to a reduced life of the chromatography system. Third, mechanical lifting equipment and significant floor and head space are required. Finally, each time a chromatography column is disassembled there are increased opportunities for unwanted contaminants to be introduced into the column, which can subsequently contaminate the fluid mixture and fraction of interest.

Another problem associated with some types of chromatography columns is the inability to clean the flow path used to introduce chromatography media into the chromatography column while maintaining a barrier between the cleaning solution and the packed chromatography media.

A known chromatography column is illustrated in FIG. 1, which employs two valves, one located at the top of the column and the other spaced from it at the bottom. Each valve has three ports. Port 1 is for feeding slurry into the column during packing and for pumping liquid into the column for reslurrying during unpacking. Port 2 is for expelling "clean" liquid pumped via port 1 to flush out the slurry line after packing, and for removal of reslurried gel during unpacking. Port 3 is the inlet and outlet for the mobile phase, and communicates directly with and only with the distribution cell.

The valves are each as shown in more detail in FIG. 2 in which a pneumatically actuated valve sleeve can assume three different positions depending upon the mode of operation. In the bottom valve during packing, the valve sleeve is in the semi-retracted packing position, as shown in FIG. 2, which closes off port 2 from communication with the inside of the column. When in this position, slurry is pumped into the column via port 1 of the bottom valve, and air or excess liquid is removed via port 2 of the top valve. When the column is purged of air, the valve sleeve of the top valve is in the closed position (i.e. fully extended into the housing).

In the run position, the valve sleeves for both the top and bottom valves are in the unactuated position, closing port 1 and port 2 of both valves from the inside of the column. When in this position, clean liquid can be pumped from port 1 to port 2 to remove any media (gel) left in the slurry line or to carry out a clean-in-place ("CIP") cycle on these lines. The column is then run by pumping mobile phase through port 3 to and from the distribution cell.

There are three methods to reslurry a packed bed employing these valves. In the first method, the bottom valve is in the fill (valve sleeve partly retracted) position and the top valve is in the drain position where the valve sleeve of the top valve is fully retracted from the column housing. When the valve sleeve of the top valve is in this position, clean liquid can be pumped via port 1 through the nozzles at the end of the tube to reslurry the gel, which is then removed through port 2. In the second method, both the bottom and top valves are in the drain position (with the sleeves fully retracted). Clean liquid is pumped into the column via port 1 of either the top or bottom valve to reslurry the gel. Reslurried material passes out through the bottom of the column. In the third method, the top valve is in the fill (sleeve partly retracted) position and the bottom valve is in the drain (sleeve fully retracted) position. This enables slurrying of the top of a packed bed and the slurry passes out of the bottom valve. All three methods can be used in combination during a reslurry operation.

To drain or empty the column, both top and bottom valves are in the drain position and either pump is reversed to withdraw liquid from the column. Alternatively, a combination of pumps may be used to inject and drain the column simultaneously through port 2 on either valve. In addition, slurry may be recycled to the column to greatly reduce the quantity of clean liquid needed to flush the column.

The above described prior art valve has a rather complex construction to ensure the sleeve adopts the required operative positions with implications for reliability and manufacturing costs. The applicant has also determined that it is possible for accidental over-pressurisation to occur during the fill operation.

The present invention seeks to provide a chromatography column which can provide the same functional capabilities of the prior art column, with a valve of reduced complexity and so more economic to manufacture, which can provide increased reliability, and can permit to the column to be vented in the event of accidental over-pressurisation.

Accordingly, the present invention provides a chromatography column including an elongated column tube having a first end and a second end spaced from said first end;

at least one valve means associated with one end which comprises a central bore, a fixed longitudinal member disposed in said central bore, said longitudinal member having a passageway and having a first port communicating with said passageway and a second port communicating with said central bore and further including a valve sleeve disposed in said central bore and movable with respect to said longitudinal member between a first position precluding communication between said first port and said column tube and between said second port and said column tube, and a second position allowing communication between said first port and said column tube and between said second port and said column tube;

the longitudinal member and valve sleeve being configured such that the central bore and passageway are always in fluid communication.

The valve has two operative positions, only, thereby allowing a reduction in the complexity of the valve. Because the central bore and passageway are always in fluid communication, should there be an accidental over-pressurization of the column during packing via the passageway in the longitudinal member, the media can enter the central bore thereby venting the column and relieving the overpressure. This is in contrast to the situation in which an over-pressurization occurs during packing with the above described prior art valve as the passageway and central bore are not in fluid communication during packing so no such venting is possible.

The chromatography column may include a column tube unit, a fixed cell assembly and an adjustable cell assembly. The column tube unit is bounded on the top or bottom by the adjustable cell assembly, and on the reverse end by the fixed cell assembly. The column tube unit holds the chromatography media once it has been introduced to the column through either the fixed cell assembly or the adjustable cell assembly.

The fixed cell assembly may incorporate the base of the column and the bottom flow distribution cell using the new valve design. The base may incorporate levelling screws to enable the column to be accurately levelled, which is essential for efficient chromatography. The bottom flow distribution cell may incorporate a minimum dead space fixed sealing arrangement whereby when the fixed cell, bed support, and column tube unit are assembled there are no unswept areas within the process flow path ensuring sanitary performance.

The adjustable cell assembly using the valve may be provided with a range of vertical adjustments to allow the position of the distribution cell to be varied in the column to achieve a range of chromatography media bed heights, and also to permit adjustment of the end cell to take up any voids that may develop during operation of the column. Adjustment of the end cell may be by any suitable means, including manual, hydraulic, electrical or pneumatic, dependent on convenience and whether the chromatographic application benefits from additional compaction. The bottom and/or top cell assembly and bed support may be coned to facilitate draining of liquid or purging of air.

The chromatography column with the fixed and adjustable cell assemblies permits the reslurrying and removal of used chromatography media and the subsequent introduction of fresh chromatography media without the time and resource-consuming step of disassembling the column. Positioning of the new valve at the top and bottom of the column allows for the process of reslurrying and removal of used chromatography media to be performed through either the top or bottom of the column depending on each user's unique needs.

The current invention uses a moveable sleeve with only two positions to perform the pack, run and unpack functions. It has been found that the pack function can be effectively performed with the sleeve fully retracted. This makes possible, as described above, the use of port 2 to be used to vent the column if inadvertently overpressurised.

BRIEF DESCRIPTION OF THE DRAWINGS

In order that the present invention may more readily be understood the following description is given, merely by way of example, with reference to the accompanying drawings, in which.

DETAILED DESCRIPTION OF THE INVENTION

Figure 1:
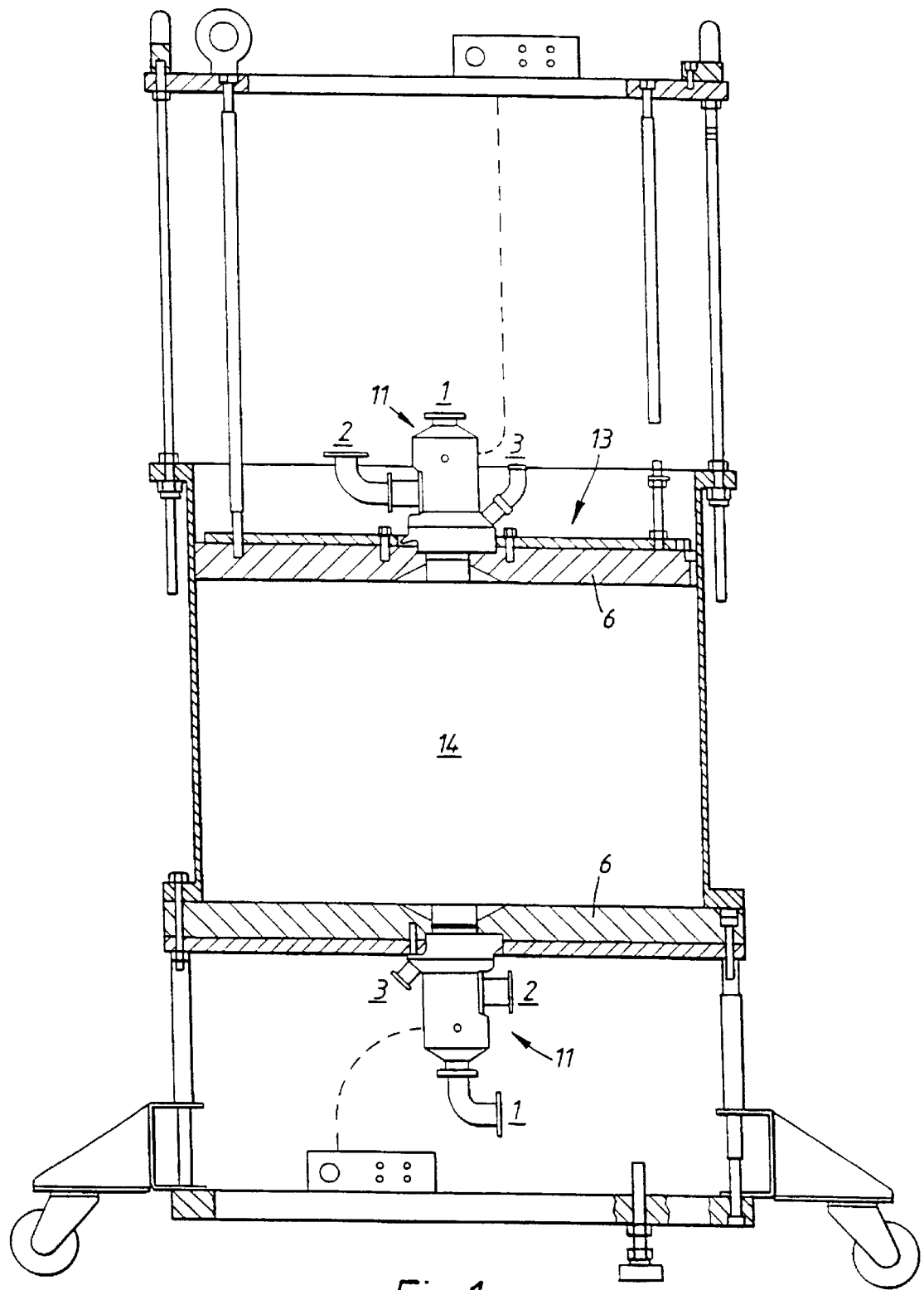
FIG. 1 is a cross section of a prior art chromatography column including a slurry valve.
Figure 2:
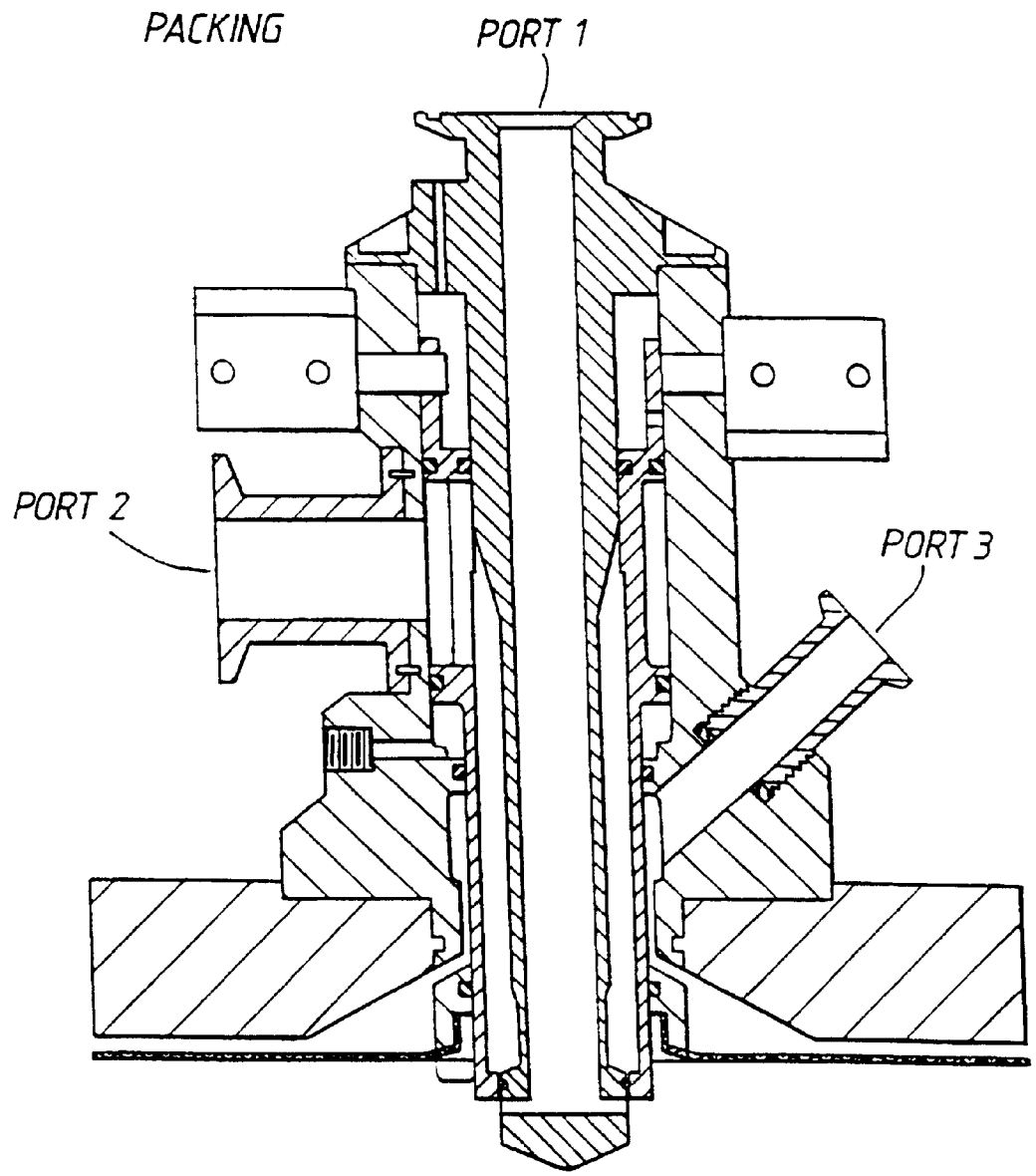
FIG. 2 is a longitudinal cross section of the prior art slurry valve of FIG. 1.
Figure 3:
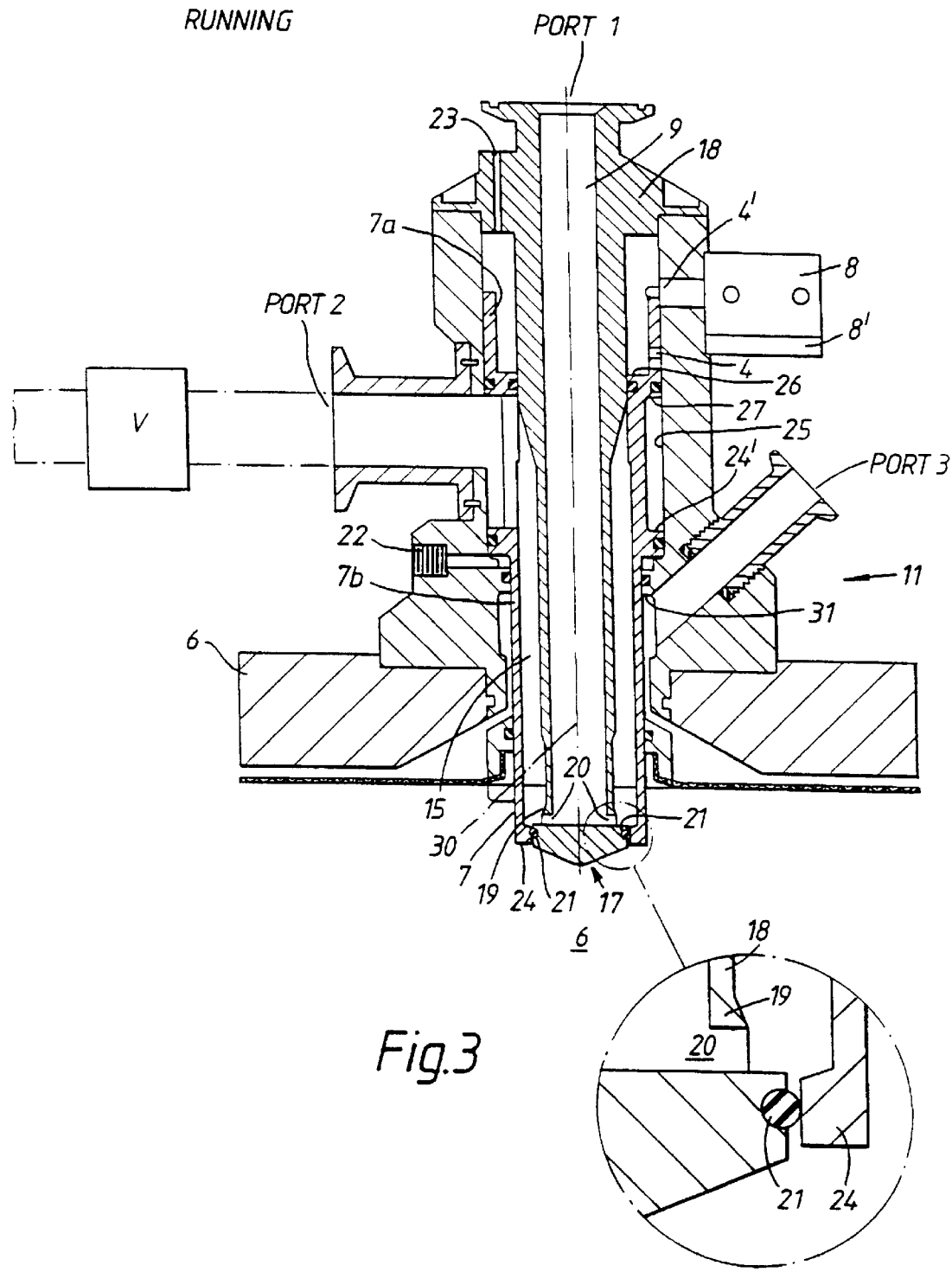
FIG. 3 is a longitudinal cross section of the chromatography column of the present invention with the slurry valve in the running position.

Referring now to the drawings, FIG. 3 shows the chromatography column fitted with two slurry valves constructed in accordance with the principles of the present invention. In the embodiment shown, the column is comprised of a top adjustable cell assembly, a hollow cylindrical housing preferably constructed of stainless steel, and a lower fixed cell assembly. Both cell assemblies have slurry valves positioned at the center. The present invention includes within its scope embodiments wherein the adjustable cell assembly is at the bottom of the column, and the fixed cell assembly is at the top.

Figure 4:
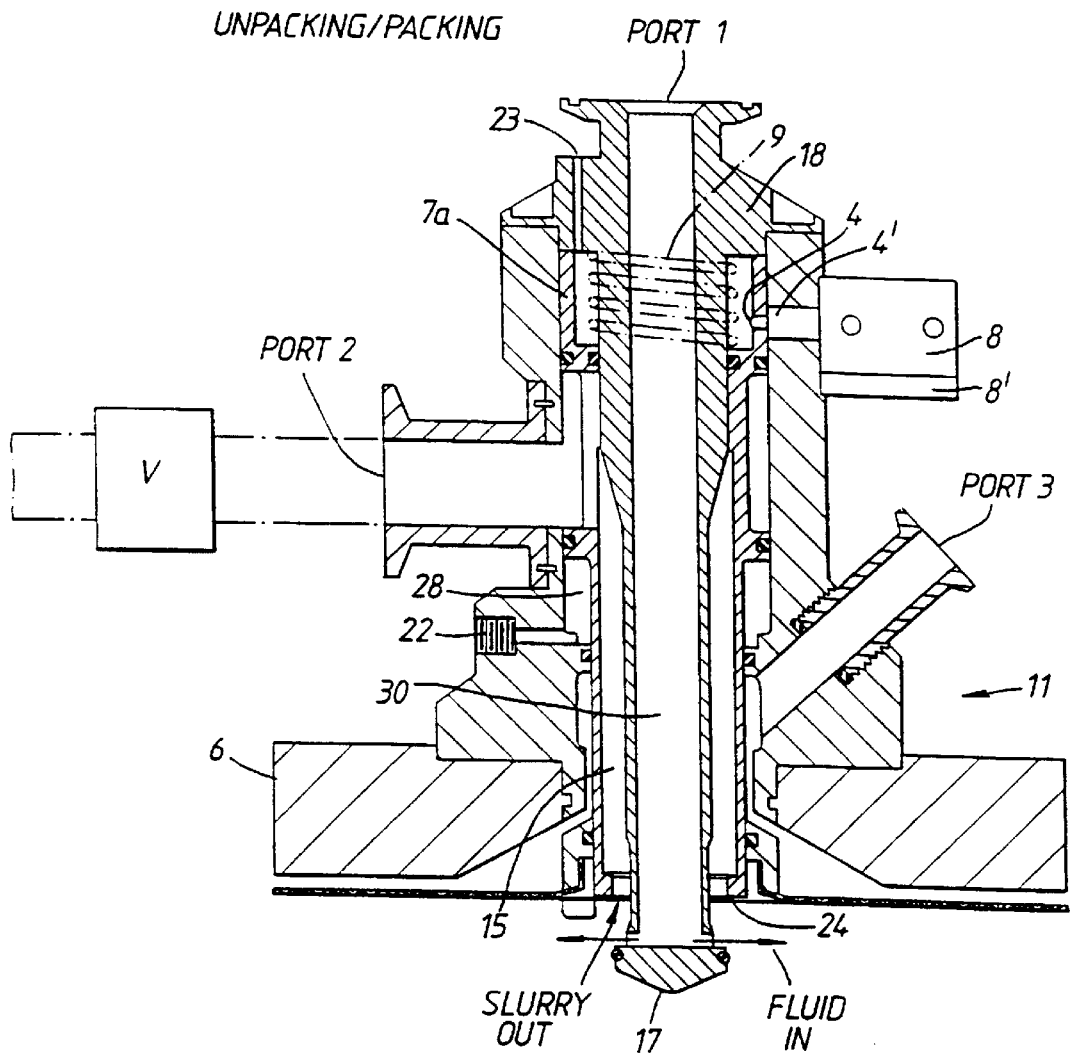
FIG. 4 is a longitudinal cross section of the chromatography column of the present invention with the slurry valve in the unpacking/packing position.

The details of the central slurry inlet/outlet valves 11 may be understood with reference to FIGS. 3 and 4. The valves comprise a housing having a central bore 15 communicating with three ports. A fixed longitudinal member 18 is located in central bore 15 and itself has a central lumen which serves as a slurry feed line 30. The slurry feed line 30 communicates at one end with port 1 and at its opposite end with the interior of the column through radially disposed passageways 20. The longitudinal member terminates in a domed head 17 that extends into the column at all times. The longitudinal member 18 has an annular portion 19 reduced in diameter to accommodate, in a sealing manner, the valve sleeve 7 as will be discussed in greater detail below.

The three ports of each of the valves 11 are used as follows: port 1 for pumping slurry through a slurry feed line 30 into the column, and for pumping liquid into the column for reslurrying during unpacking; port 2 for removal of reslurried gel during unpacking; and port 3 which is the inlet and outlet for the mobile phase, this port communicating directly with, and only with, the distribution cell 6.

Ports 1 and 2 may be closed off from the column by means of an annular valve sleeve 7 slidably positioned in the central bore 15. The valve sleeve 7 includes a top portion 7a, which is L-shaped in cross-section. The top portion 7a includes a pin hole 4 for receiving pin 4' in order to lock the valve sleeve 7 in its raised position as shown in FIG. 4. The valve sleeve 7 also includes an annular lower portion 7b. The bottom end of the lower portion 7b includes an annular lip 24 adapted to seal against the head 17 in the running position (FIG. 3). The annular lip 24 and longitudinal member 18 are dimensioned such that as the seal between lip 24 and longitudinal member 18 is broken a gap is created with the annular reduced diameter portion 19 of the longitudinal member, so as to provide fluid communication between the central bore 15 and the passageway 9 to the column interior simultaneously as the seal between the sleeve 7 and annular lip 24 is broken. The valve sleeve 7 may be actuated by any suitable means, such as manually, or electrically, or hydraulically, or preferably pneumatically.

In this embodiment the sleeve 7 is driven axially by application of compressed air through either of two pneumatic ports 22 and 23.

In particular, the sleeve 7 has an outwardly extending land 24' slidable within a cylindrical wall portion 25 of the valve body, and an inwardly extending land 26 and an outwardly extending land 27 at the same axial positions just above the port 2, such that the outwardly extending land 27 slides along the same cylindrical surface 25 of the valve body and the inwardly extending land 26 slides along a cylindrical exterior of a top part of the fixed body 18 of the valve.

Below the land 24' of the sleeve 7, the valve housing has an inwardly extending land 31 which will be fixed in position and which, together with the land 24 on the moving valve sleeve 7, defines a fluid pressure chamber portion 28 of the central bore, isolated from another chamber portion 29 into which the third port 3 opens and which communicates with the distribution cell 6.

The inner pneumatic port 22 thus provides a means of applying pressure to the sealed space 28 below the land 24 for the purposes of retracting the sleeve 7 (moving it relatively outwardly from the FIG. 3 position). Similarly application of compressed air to the outer pneumatic port 23 applies pressure above the twin lands 26 and 27 and drives the sleeve 7 axially inwardly (inwardly from the FIG. 4 position). In this manner the axial movement of the sleeve can be effected.

However, this pneumatically activated axial movement of the sleeve 7 is required to cause it to occupy one of two different positions and these positions are defined by virtue of the pin 4' which co-operates with the hole 4 of the valve sleeve 7.

FIG. 4 shows the "packing" position in which slurry can be discharged from the head 17 of the fixed longitudinal member 18 by virtue of retraction of the sleeve 7 outwardly (to the FIG. 4 position) so that it exposes the nozzles 20 of the head 17. In this position the pin 4' must be retracted before being extended once more. By positively checking that the pin 4' driven by the actuator 8 extends again into hole 4 there is achieved a feedback which confirms that the sleeve is in the "packing" position. This positioning of the pin 4' in the actuators 8 is checked by virtue of reed switch 8' of the actuator.

When the valve sleeve 7 is to be extended to the "running" position for the purposes of leaving valve port 3, only, open to the media in the bed by way of the filter mesh of the distribution cell 6, the pin 4' must be retracted in order to allow the sleeve 7 to pass inwardly to the FIG. 3 position. The pin 4' is then driven by the actuator 8 to extend above the top rim of the valve sleeve 7 to hold it firmly in the "Running" (FIG. 3) position. Positive feedback checking of the position of the valve is derived by checking that pin 4' is extended, again using the reed switch 8'.

When finally the valve sleeve 7 is to be fully retracted, again, to the "unpacking" position shown in FIG. 4 it reaches a fully raised position as viewed in FIG. 4 and pin 4' can now engage in its hole 4 so that the positive feedback checking action by the reed switches 8' checks that the pin 4' is advanced.

If the pneumatic control system energising the actuator 8 fails to detect that the pin 4' is advanced when the "unpacking/packing" position of FIG. 4 has been selected then there will be a malfunction indicated to show that the valve is not fully open. Likewise, if in the FIG. 3 position the pin 4' is not confirmed as being fully extended then again a malfunction will be indicated to show that the sleeve has not descended to the "running" position of FIG. 3.

The valve is thus positively driven outwardly and inwardly and the location of it is each of its two positions is confirmed by the pin 4' driven by the actuator 8 and checked by the reed switch 8' of this actuator.

Additionally the valve member may be biased axially (in this case inwardly as viewed in FIG. 4) by an optional helical compression spring 9 around the fixed longitudinal member 18 and pressing inwardly against the inwardly directed land 26 of the valve sleeve. Thus the default position, when the air supply 10 is disconnected from the pneumatic control circuit after packing or for storage, is the "Running" FIG. 3 position, closing ports 1 and 2 off from the column. This occurs when the air pressure at pneumatic port 23, and optionally the force of spring 9, forces the valve sleeve 7 to the closed position (FIG. 3). As indicated above, the valve sleeve 7 is held in closed position both by the axial forces and the locking pin 4' of the pneumatic actuator 8 being extended above the top of the sleeve. This prevents the sleeve 7 from opening inadvertently or due to operating pressure in the column. Those skilled in the art will understand that the description of a pneumatically actuated valve sleeve is for illustrative purposes only; the claims set forth below are intended to encompass any means for actuating the valve operation, including both automated, electrical pneumatic valve opening and/or closing, as well as manually actuated adjustments to the positioning of the valve sleeve 7.

The pneumatic control circuit to operate the actuator 8 will be readily apparent to the man skilled in the art and is not described herein in detail.

One typical operation of the inlet/outlet slurry valves 11 is as follows. Starting from the unpacking position shown in FIG. 4, the lower slurry valve 11 remains in the same position as shown in FIG. 4. Port 2 is isolated external to the device possibly by means of any known pressure relief device V. In this position both ports 1 and 2 communicate with the internals of the column 6.

The inclusion of a pressure relief device in-line with port 2 during the packing operation provides a means for venting the column 6 in the event of incorrect operation.

The top slurry valve 11 must then be placed in the "running" (FIG. 3 position) which requires the actuator 8 to withdraw the pin 4' from the hole 4, allowing the pneumatic pressure on the outer pneumatic port 23 to drive the sleeve inwardly until the FIG. 3 position is attained. At this point the actuator 8 is then operated to advance the pin 4' so it sits just above the axially outer rim of the valve sleeve 7 and holds the sleeve against retraction from the FIG. 3 position.

In this position, the annular lip 24 of the top valve 11 seals against the head 17, thus closing ports 1 and 2 from the column 6. Slurry is fed, for example by a pump, through port 1 of the bottom slurry valve 11 and the slurry feed line 30 into the column. The chromatography media is retained in the column by the distribution cell 6 of the adjustable cell assembly 13, while air and the liquid forming the slurry with the chromatography media are removed, initially venting through port 2 of the top valve 11 until the column is purged of air, and subsequently through port 3 of the top slurry valve 11.

When the packing of the column with chromatography media 14 is complete, the pneumatic control circuit places the valve sleeve 7 of the bottom slurry valve 11 into the closed/running position (FIG. 3) in the manner just described for the top valve 11, thus closing off ports 1 and 2 from the column. This creates a flow path through slurry feed line 30 and central bore 15 from port 1 to port 2 of each valve 11, through which a cleaning solution can be fed, for example by a pump, to clean in place each port 1, port 2, and slurry feed line 30. This cleaning operation can be performed at the same time as processing of the liquid to be separated to prevent the settling and hardening of any residual chromatography media 14 in the slurry feed line 30. This operation of cleaning can be made to automatically follow setting the slurry valve to running position for operator convenience.

The chromatography column is now ready to separate the mixture of interest. The mixture (mobile phase) to be separated is fed, for example by a pump (not shown), through port 3 of either the top or bottom slurry valve 11 into the column through the distribution cell 6 and then flows through the chromatography media 14 and is removed through port 3 of the other slurry valve 11.

After the mixture of interest has been separated, or if for any other reason, it becomes necessary or desirable to reslurry and remove the chromatography media 14, the top slurry valve 11 and the bottom slurry valve 11 are both placed in the unpacking position (FIG. 4), where each pin 4' is engaged in pin hole 4. This causes the bottom portion 7b of the valve sleeve to be fully retracted, allowing communication between the column interior and the central bore 15. This unpacking position is achieved from the running position by firstly operating the actuator 8 to retract the pin 4' from the hole 4, and then applying pressure to the inner pneumatic port 22 to retract the valve sleeve 7 (and in so doing overcome the spring force of the optional spring 9) until the end position of travel is reached where the sleeve 7 is fully retracted. At this point the actuator 21 can operate to advance pin 4' into the hole 4 of the sleeve. Only when this pin has been advanced is there attainment of the positive feedback signal from the reed switch 8'.

Clean liquid is initially introduced into the column (such as by a pump) via port 1 of the bottom slurry valve 11, which reslurries the chromatography media 14 which is removed through port 2 of the bottom slurry valve. Removal of chromatography media slurry by port 2 may be assisted by a second pump (not shown) in which case the top slurry valve 11 is placed in the unpacking position. The clean liquid is then switched to be introduced via port 1 of the top valve. The effect is to wash out a core of packed chromatography media from near the top valve and from near the bottom valve. An additional but optional method of unpacking is the backflush through the filter mesh of the lower distribution cell 6 to fluidize the media (gel) to assist draining of slurry from the column.

After a short period the dilute slurry washed from the column can be recycled to the port 1 of the top valve in place of clean liquid, thereby reducing the quantity of clean liquid required.

Clean liquid or a sanitizing agent may be used for the final flushing of the column. The use of a slurry valve 11 on both the top and bottom cell assemblies facilitates the loading and removal of chromatography media 14 through either the top or bottom of the column. Another benefit of using a slurry valve 11 on both the top and bottom cell assemblies is the ability to flow the mixture to be separated in either a top-to-bottom, or bottom-to-top flow path. By judicial use of slurry or fresh buffer, it is possible to minimize the volume of liquid needed to re-slurry the contents of the column and empty the column of gel. It is understood that the use of two valves in the preferred embodiment is meant for the purposes of illustrating many of the versatile uses of the valve, and is not meant as a limitation. Those skilled in the art will realize that it is possible to use only one slurry valve, on either the top or bottom cell assembly, although the performance options would be more limiting. All such modifications which do not depart from the spirit of the invention are intended to be included within the scope of the appended claims.

Particular regard has been made to the cleanability of the valve. Sanitary design has been applied to the type of hose couplings, material selection and finish, sealing technology and method for cleaning in place (CIP). The valve may be cleaned in place when in the running position (FIG. 3), leaving no unswept surfaces. The profile, location, number and material used for the seals 21 is particularly important. Suitable materials include EPDM, PTFE or composite materials for the seal material.

Once the internal passages through ports 2 and 1 have been cleaned in place, the valve can either be blown through with air or left full with fluid, and all connections for pneumatic actuation and slurry process lines can be disconnected. This enables the column to either be stored or operated in the running FIG. 3 position, without attachment to a station for transferring slurry to or from the column.

The pneumatic control circuit provides positive locking positions for each of the three positions of the valve sleeve 7 and positive feedback confirmation of those positions. By use of positional indicators on the pneumatic control circuit, it is possible to provide affirmative feedback of the sleeve position to provide operator validation information. One indicator is used for this in the preferred embodiment, but more can be used as will be readily appreciated by those skilled in the art.

What is claimed is:

1. A chromatography column, comprising:

an elongated column tube having a first end and a second end spaced from said first end;

at least one valve means associated with one end which comprises a central bore, a fixed longitudinal member disposed in said central bore, said longitudinal member having a passageway and having a first port communicating with said passageway and a second port communicating with said central bore and further including a valve sleeve disposed in said central bore and movable with respect to said longitudinal member between a first position precluding communication between said first port and said column tube and between said second port and said column tube, and a second position allowing communication between said first port and said column tube and between said second port and said column tube;

the longitudinal member and valve sleeve being configured such that the central bore and passageway are always in fluid communication.

2. The chromatography column of claim 1, wherein said valve sleeve is pneumatically actuated for movement between said first and second positions.

3. The chromatography column of claim 2, wherein said longitudinal member terminates at one end in a head disposed in said column.

4. The chromatography column of claim 2, wherein said valve sleeve seals against said head when in said first position.

5. The chromatography column of claim 2, wherein said longitudinal member comprises a portion reduced in diameter, and wherein said valve sleeve terminates in an annular lip, the dimensions of said annular lip being such that a gap is formed between said annular lip and said portion reduced in diameter when said valve sleeve is not in said first position.

6. The chromatography column of claim 2, wherein said valve sleeve envelops said longitudinal member.

7. The chromatography column as claimed in claim 2 in which there are two valve means, each associated with a respective one of said first end and said second end of said chromatography valve.

8. The chromatography column of claim 2 including a valve means to open and close the second port.

9. The chromatography column of claim 1, wherein said longitudinal member terminates at one end in a head disposed in said column.

10. The chromatography column of claim 1, wherein said valve sleeve seals against said head when in said first position.

11. The chromatography column of claim 1, wherein said longitudinal member comprises a portion reduced in diameter, and wherein said valve sleeve terminates in an annular lip, the dimensions of said annular lip being such that a gap is formed between said annular lip and said portion reduced in diameter when said valve sleeve is not in said first position.

12. The chromatography column of claim 1, wherein said valve sleeve envelops said longitudinal member.

13. The chromatography column as claimed in claim 1 in which there are two valve means, each associated with a respective one of said first end and said second end of said chromatography valve.

14. The chromatography column of claim 1 including a valve means to open and the second port.

15. A method of packing a chromatography column as claimed in claim 14 in which the second port is opened in the event over-pressurisation of the column tube is detected.

* * * * *